(12) United States Patent
Fukui et al.

(10) Patent No.: US 8,106,178 B2
(45) Date of Patent: Jan. 31, 2012

(54) PROBE, PROBE SET, PROBE-IMMOBILIZED CARRIER, AND GENETIC TESTING METHOD

(75) Inventors: Toshifumi Fukui, Yokohama (JP); Hiroto Yoshii, Tokyo (JP); Hideto Kuribayashi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 1024 days.

(21) Appl. No.: 11/935,789

(22) Filed: Nov. 6, 2007

(65) Prior Publication Data

US 2009/0130667 A1    May 21, 2009

(30) Foreign Application Priority Data

Nov. 10, 2006 (JP) ................. 2006-306006

(51) Int. Cl.
*C07H 21/04* (2006.01)
*C12Q 1/68* (2006.01)

(52) U.S. Cl. ..................... 536/24.32; 435/6.1

(58) Field of Classification Search .................. None
See application file for complete search history.

(56) References Cited

U.S. PATENT DOCUMENTS

| | | | |
|---|---|---|---|
| 5,512,446 A | 4/1996 | Miyazaki et al. | |
| 5,700,647 A | 12/1997 | Miyazaki et al. | |
| 5,846,730 A | 12/1998 | Miyazaki et al. | |
| 6,582,908 B2 * | 6/2003 | Fodor et al. | 506/9 |
| 7,091,031 B2 * | 8/2006 | Cheng et al. | 435/252.3 |
| 2004/0181048 A1 * | 9/2004 | Wang | 536/24.3 |
| 2004/0241643 A1 | 12/2004 | Yamamoto et al. | |
| 2005/0164217 A1 | 7/2005 | Yoshii | |
| 2007/0105100 A1 | 5/2007 | Yoshii et al. | |
| 2007/0134702 A1 | 6/2007 | Fukui et al. | |
| 2008/0113363 A1 | 5/2008 | Fukui et al. | |
| 2008/0113364 A1 | 5/2008 | Fukui et al. | |
| 2008/0113365 A1 | 5/2008 | Kuribayashi et al. | |
| 2008/0124733 A1 | 5/2008 | Fukui et al. | |

FOREIGN PATENT DOCUMENTS

| | | |
|---|---|---|
| JP | 8-89254 | 4/1996 |
| JP | 2004-313181 | 11/2004 |
| JP | 2006-129828 | 5/2006 |

OTHER PUBLICATIONS

Ludwig et al. (FEMS Micro. 1990, 71, p. 139-144, IDS reference).*
Ezaki et al. (Int. J. Syst. Bact., 1994, 44(1), 130-136).*
Buck et al. (Biotechniques, 1999, 27(3):528-536).*
U.S. Appl. No. 11/996,744, International filing date Aug. 4, 2006, Yoshii.
U.S. Appl. No. 11/935,930, filed Nov. 6, 2007, Yoshii, et al.
U.S. Appl. No. 11/935,807, filed Nov. 6, 2007, Kuribayashi, et al.
U.S. Appl. No. 11/935,914, filed Nov. 6, 2007, Kuribayashi, et al.
U.S. Appl. No. 11/935,746, filed Nov. 6, 2007, Yoshii, et al.
U.S. Appl. No. 11/935,820, filed Nov. 6, 2007, Kuribayashi, et al.
U.S. Appl. No. 11/935,849, filed Nov. 6, 2007, Yoshii, et al.
European Search Report dated Apr. 2, 2008 in European Application No. 07021833.4.
Wolfgang Ludwig, et al., "The phylogenetic position of *Peptococcus niger* based on 16S rRNA sequence studies", FEMS Microbiology Letters, vol. 71, 1990, pp. 139-144.
Database Genbank [Online], Sep. 4, 1991, "*Peptococcus niger* DNA for 16S ribosomal RNA", Genbank, accession No. X55797, Dababase accession No. gi:45659.

* cited by examiner

*Primary Examiner* — Stephanie K Mummert
(74) *Attorney, Agent, or Firm* — Fitzpatrick, Cella, Harper & Scinto

(57) ABSTRACT

A nucleic acid probe for classification of pathogenic bacterial species is capable of collectively detecting bacterial strains of the same species and differentially detecting them from other bacterial species. Any one of the base sequences of SEQ ID NOS. 81 to 83 and complementary or modified sequences thereof or a combination of at least two of them is used for detecting the gene of an infectious disease pathogenic bacterium.

11 Claims, 1 Drawing Sheet

PROBE, PROBE SET, PROBE-IMMOBILIZED CARRIER, AND GENETIC TESTING METHOD

BACKGROUND OF THE INVENTION

1. Field of the Invention

The present invention relates to a probe and a probe set for detecting a gene of infectious disease pathogenic bacterium, *Peptococcus niger*, which are useful for detection and identification of the causative organism of an infectious disease, a probe-immobilized carrier on which the probe or the probe set is immobilized, a genetic testing method using the probe-immobilized carrier, and a genetic testing kit to be used for the method.

2. Description of the Related Art

Heretofore, reagents for and methods of quickly and accurately detecting the causative organisms of infectious diseases in analytes have been proposed. For instance, Japanese Patent Application Laid-Open No. H08-089254 discloses oligonucleotides having specific base sequences, which can be respectively used as probes and primers for detecting pathogenic bacteria of candidiasis and aspergillosis, and a method of detecting target bacteria using such oligonucleotides. In addition, the same patent document also discloses a set of primers used for concurrently amplifying a plurality of target bacteria by PCR. In other words, those primers are used for the PCR amplification of nucleic acid fragments from fungi, which serve as a plurality of targets, in an analyte. Target fungal species in the analyte can be identified by detecting the presence of a specific part of the sequence by a hybridization assay using probes specific to the respective fungi and the nucleic acid fragments amplified by the respective primers.

On the other hand, the method to use probe array in which probes having sequences complementary to the respective base sequences are arranged at intervals on a solid support is known as a method capable of simultaneously detecting a plurality of oligonucleotides having different base sequences. (Japanese Patent Application Laid-Open No. 2004-313181).

SUMMARY OF THE INVENTION

However, it is no easy task to design a probe for specifically detecting a gene of an infectious disease pathogenic bacterium in a sample. That is, as well as the target gene, the sample may further contain genes of other infectious disease pathogenic bacteria. Thus, it is no easy task to design the probe that specifically detects the gene of the infectious disease pathogenic bacterium while suppressing the cross contamination which is the influence of the presence of the genes of other infectious disease pathogenic bacteria. Under such circumstances, the inventors of the present invention have studied for obtaining a probe which allows accurate detection of a gene of an infectious disease pathogenic bacterium as mentioned hereinbelow while maintaining the cross contamination level low even when a sample in which genes of different bacteria are present is used. As a result, the inventors of the present invention have finally found a plurality of probes capable of precisely detecting the gene of the infectious disease pathogenic bacterium, *Peptococcus niger*.

A first object of the present invention is to provide a probe and a probe set, which can precisely identify a gene of a target bacterium from an analyte in which various bacteria are concurrently present. Another object of the present invention is to provide a probe-immobilized carrier which can be used for precisely identifying a target bacterium from an analyte in which various bacteria are concurrently present. Still another object of the present invention is to provide a genetic testing method for detecting a target bacterium, which can quickly and precisely detect the target bacterium from various bacteria in an analyte when they are present therein, and a kit for such a method.

The probe for detecting a gene of infectious disease pathogenic bacterium, *Peptococcus niger*, of the present invention has any one of the following base sequences (1) to (4):

(1) GTACCTGTAAGAAAGACGGCCTTCGT (SEQ ID NO. 81) or a complementary sequence thereof;
(2) CTGCCGAGTGATGTAATGTCACTTTTC (SEQ ID NO. 82) or a complementary sequence thereof;
(3) TCGGAGGTTTCAAGACCGTCGG (SEQ ID NO. 83) or a complementary sequence thereof; and
(4) a modified sequence prepared such that any one of the sequences of SEQ ID NOS. 81 to 83 and the complementary sequences thereof is subjected to base deletion, substitution, or addition as far as the modified sequence retains a function as the probe.

In addition, the probe set for detecting a gene of infectious disease pathogenic bacterium, *Peptococcus niger*, of the present invention includes at least two probes selected from the following items (A) to (L):

(A) a probe having a base sequence represented by GTACCTGTAAGAAAGACGGCCTTCGT (SEQ ID NO. 81);
(B) a probe having a base sequence represented by CTGCCGAGTGATGTAATGTCACTTTTC (SEQ ID NO. 82);
(C) a probe having a base sequence represented by TCGGAGGTTTCAAGACCGTCGG (SEQ ID NO. 83);
(D) a probe having a complementary sequence of the base sequence represented by SEQ ID NO. 81;
(E) a probe having a complementary sequence of the base sequence represented by SEQ ID NO. 82;
(F) a probe having a complementary sequence of the base sequence represented by SEQ ID NO. 83;
(G) a probe having a modified sequence obtained by base deletion, substitution, or addition on the base sequence represented by SEQ ID NO. 81 as far as it retains the function of a probe for detecting the gene of *Peptococcus niger*;
(H) a probe having a modified sequence obtained by base deletion, substitution, or addition on the base sequence represented by SEQ ID NO. 82 as far as it retains the function of a probe for detecting the gene of *Peptococcus niger*;
(I) a probe having a modified sequence obtained by base deletion, substitution, or addition on the base sequence represented by SEQ ID NO. 83 as far as it retains the function of a probe for detecting the gene of *Peptococcus niger*;
(J) a probe having a modified sequence obtained by base deletion, substitution, or addition on the complementary sequence of the base sequence represented by SEQ ID NO. 81 as far as it retains the function of a probe for detecting the gene of *Peptococcus niger*;
(K) a probe having a modified sequence obtained by base deletion, substitution, or addition on the complementary sequence of the base sequence represented by SEQ ID NO. 82 as far as it retains the function of a probe for detecting the gene of *Peptococcus niger*; and
(L) a probe having a modified sequence obtained by base deletion, substitution, or addition on the complementary sequence of the base sequence represented by SEQ ID NO. 83 as far as it retains the function of a probe for detecting the gene of *Peptococcus niger*.

The characteristic feature of the probe-immobilized carrier of the present invention is that at least one of the above-mentioned probes (A) to (L) is immobilized on a solid-phase carrier, and when a plurality of probes are employed, the respective probes are arranged at intervals.

The method of detecting a gene of an infectious disease pathogenic bacterium, *Peptococcus niger*, in an analyte by using a probe-immobilized carrier of the present invention includes the steps of: (i) reacting the analyte with the probe-immobilized carrier having the above-mentioned constitution; and (ii) detecting the presence or absence of a reaction of the probe on the probe-immobilized carrier with a nucleic acid in the analyte, or detecting the strength of a hybridization reaction of the probe on the probe-immobilized carrier with a nucleic acid in the analyte.

The characteristic feature of the kit for detecting an infectious disease pathogenic bacterium, *Peptococcus niger*, of the present invention is to include at least one of the above-mentioned probes (A) to (L), and a reagent for detecting a reaction between the probe and a target nucleic acid.

According to the present invention, when an analyte is infected with the above-mentioned causative bacterium, the bacterium can be more quickly and precisely identified from the analyte even if the analyte is simultaneously and complexly infected with other bacteria in addition to the above-mentioned bacterium. In particular, *Peptococcus niger* can be detected while precisely distinguishing it from *Escherichia coli* which may otherwise cause cross contamination.

Further features of the present invention will become apparent from the following description of exemplary embodiments with reference to the attached drawings.

DESCRIPTION OF THE EMBODIMENTS

Figure 1:
FIG. 1 is a diagram illustrating a 1st PCR protocol.

The inventors of the present invention have obtained almost all of bacteria (represented by (1) to (80) below), which have been known as septicemia pathogenic bacteria so far, from the respective depository institutions and identified the 16S rRNA gene sequences of all the bacteria.

Subsequently, while making a comparison of all the identified sequences, probe sequences for *Peptococcus niger* were investigated in detail and the probes of the present invention, which can identify *Peptococcus niger*, have finally been found out.

| (1) *Staphylococcus aureus* | (ATCC12600) |
|---|---|
| (2) *Staphylococcus epidermidis* | (ATCC14990) |
| (3) *Escherichia coli* | (ATCC11775) |
| (4) *Klebsiella pneumoniae* | (ATCC13883) |
| (5) *Pseudomonas aeruginosa* | (ATCC10145) |
| (6) *Serratia marcescens* | (ATCC13380) |
| (7) *Streptococcus pneumoniae* | (ATCC33400) |
| (8) *Haemophilus influenzae* | (ATCC33391) |
| (9) *Enterobacter cloacae* | (ATCC13047) |
| (10) *Enterococcus faecalis* | (ATCC19433) |
| (11) *Staphylococcus haemolyticus* | (ATCC29970) |
| (12) *Staphylococcus hominis* | (ATCC27844) |
| (13) *Staphylococcus saprophyticus* | (ATCC15305) |
| (14) *Streptococcus agalactiae* | (ATCC13813) |
| (15) *Streptococcus mutans* | (ATCC25175) |
| (16) *Streptococcus pyogenes* | (ATCC12344) |
| (17) *Streptococcus sanguinis* | (ATCC10556) |
| (18) *Enterococcus avium* | (JCM8722) |
| (19) *Enterococcus faecium* | (ATCC19434) |
| (20) *Pseudomonas fluorescens* | (ATCC13525) |
| (21) *Pseudomonas putida* | (ATCC12633) |
| (22) *Burkholderia cepacia* | (JCM5964) |
| (23) *Stenotrophomonas maltophilia* | (ATCC13637) |
| (24) *Acinetobacter baumannii* | (ATCC19606) |
| (25) *Acinetobacter calcoaceticus* | (ATCC23055) |
| (26) *Achromobacter xylosoxidans* | (ATCC27061) |
| (27) *Vibrio vulnificus* | (ATCC27562) |
| (28) *Salmonella choleraesuis* | (JCM1651) |
| (29) *Citrobacter freundii* | (ATCC8090) |
| (30) *Klebsiella oxytoca* | (ATCC13182) |
| (31) *Enterobacter aerogenes* | (ATCC13048) |
| (32) *Hafnia alvei* | (ATCC13337) |
| (33) *Serratia liquefaciens* | (ATCC27592) |
| (34) *Proteus mirabilis* | (ATCC29906) |
| (35) *Proteus vulgaris* | (ATCC33420) |
| (36) *Morganella morganii* | (ATCC25830) |
| (37) *Providencia rettgeri* | (JCM1675) |
| (38) *Aeromonas hydrophila* | (JCM1027) |
| (39) *Aeromonas sobria* | (ATCC43979) |
| (40) *Gardnerella vaginalis* | (ATCC14018) |
| (41) *Corynebacterium diphtheriae* | (ATCC2701) |
| (42) *Legionella pneumophila* | (ATCC33152) |
| (43) *Bacillus cereus* | (ATCC14579) |
| (44) *Bacillus subtilis* | (ATCC6051) |
| (45) *Mycobacterium kansasii* | (ATCC12478) |
| (46) *Mycobacterium intracellulare* | (ATCC13950) |
| (47) *Mycobacterium chelonae* | (ATCC35752) |
| (48) *Nocardia asteroids* | (ATCC19247) |
| (49) *Bacteroides fragilis* | (JCM11019) |
| (50) *Bacteroides thetaiotaomicron* | (JCM5827) |
| (51) *Clostridium difficile* | (ATCC51695) |
| (52) *Clostridium perfringens* | (JCM1290) |
| (53) *Eggerthella lenta* | (JCM10763) |
| (54) *Fusobacterium necrophorum* | (JCM3718) |
| (55) *Fusobacterium nucleatum* | (ATCC25586) |
| (56) *Lactobacillus acidophilus* | (ATCC4356) |
| (57) *Anaerococcus prevotii* | (JCM6490) |
| (58) *Peptoniphilus asaccharolyticus* | (JCM8143) |
| (59) *Porphyromonas asaccharolytica* | (JCM6326) |
| (60) *Porphyromonas gingivalis* | (JCM8525) |
| (61) *Prevotella denticola* | (ATCC38184) |
| (62) *Propionibacterium acnes* | (JCM6473) |
| (63) *Acinetobacter johnsonii* | (ATCC17909) |
| (64) *Acinetobacter junii* | (ATCC17908) |
| (65) *Aeromonas schubertii* | (ATCC43700) |
| (66) *Aeromonas veronii* | (ATCC35624) |
| (67) *Bacteroides distasonis* | (ATCC8503) |
| (68) *Bacteroides vulgatus* | (ATCC8482) |
| (69) *Campylobacter coli* | (ATCC33559) |
| (70) *Campylobacter hyointestinalis* | (ATCC35217) |
| (71) *Campylobacter jejuni* | (ATCC33560) |
| (72) *Flavobacterium aquatile* | (ATCC11947) |
| (73) *Flavobacterium mizutaii* | (ATCC33299) |
| (74) *Peptococcus niger* | (ATCC27731) |
| (75) *Propionibacterium avidum* | (ATCC25577) |
| (76) *Propionibacterium freudenreichii* | (ATCC6207) |
| (77) *Propionibacterium granulosum* | (ATCC25564) |
| (78) *Clostridium butyricum* | (ATCC13949) |
| (79) *Flavobacterium hydatis* | (NBRC14958) |
| (80) *Flavobacterium johnsoniae* | (NBRC14942) |

The deposition numbers of the bacterial species obtained are shown in the respective parentheses on the right side in the above. Bacterial species having deposition numbers beginning with "ATCC", "JCM" and "NBRC" are available from American Type Culture Collection, Japan Collection of Microorganisms (RIKEN BioResource Center) and National Board for Respiratory Care, respectively.

The present invention provides an oligonucleotide probe for identifying an infectious disease pathogenic bacterium (hereinafter, simply referred to as a probe) and a probe set including a combination of two or more probes. The use of such a probe or a probe set allows the detection of the following bacterium which will cause inflammation by infection.

[Bacterial Name]
*Peptococcus niger*

That is, the probe of the present invention can detect the 16S rRNA gene sequence among genes of the above-mentioned bacterium, having the following sequences: (A) a probe having a base sequence represented by GTACCTG-TAAGAAAGACGGCCTTCGT (SEQ ID NO. 81); (B) a probe having a base sequence represented by CTGCCGAGT-GATGTAATGTCACTTTTC (SEQ ID NO. 82); (C) a probe having a base sequence represented by TCGGAG-GTTTCAAGACCGTCGG (SEQ ID NO. 83); (D) a probe having a complementary sequence of the base sequence represented by SEQ ID NO. 81; (E) a probe having a complementary sequence of the base sequence represented by SEQ ID NO. 82; (F) a probe having a complementary sequence of the base sequence represented by SEQ ID NO. 83; (G) a probe having a modified sequence obtained by base deletion, substitution, or addition on the base sequence represented by SEQ ID NO. 81 as far as it retains the function of a probe for detecting the gene of *Peptococcus niger*; (H) a probe having a modified sequence obtained by base deletion, substitution, or addition on the base sequence represented by SEQ ID NO. 82 as far as it retains the function of a probe for detecting the gene of *Peptococcus niger*; (I) a probe having a modified sequence obtained by base deletion, substitution, or addition on the base sequence represented by SEQ ID NO. 83 as far as it retains the function of a probe for detecting the gene of *Peptococcus niger*; (J) a probe having a modified sequence obtained by base deletion, substitution, or addition on the complementary sequence of the base sequence represented by SEQ ID NO. 81 as far as it retains the function of a probe for detecting the gene of *Peptococcus niger*; (K) a probe having a modified sequence obtained by base deletion, substitution, or addition on the complementary sequence of the base sequence represented by SEQ ID NO. 82 as far as it retains the function of a probe for detecting the gene of *Peptococcus niger*; and (L) a probe having a modified sequence obtained by base deletion, substitution, or addition on the complementary sequence of the base sequence represented by SEQ ID NO. 83 as far as it retains the function of a probe for detecting the gene of *Peptococcus niger*.

The probe set can be formed using at least two of those probes.

The functions of those probes significantly depend on the specificity of each probe sequence corresponding to the target nucleic acid sequence of interest. The specificity of a probe sequence can be evaluated from the degree of coincidence of bases with the target nucleic acid sequence and the probe sequence. Further, when a plurality of probes constitute a probe set, the variance of melting temperatures among the probes may affect the performance of the probe set.

For designing a probe sequence, a region showing a high specificity to a specific bacterial species of interest regardless of any differences in strain is selected. The region contains three or more bases which are not coincident with corresponding bases in the sequences of any other bacterial species. The probe sequence is designed so that the melting temperature between the probe sequence and the corresponding sequence of the specific bacterial species of interest will differ by 10° C. or more from the melting temperatures between the probe sequence and the corresponding sequences of any other bacterial species. Further, one or more bases can be deleted or added so that the respective probes immobilized on a single carrier may have melting temperatures within a predetermined range.

The inventors of the present invention found out by experiments that the hybridization intensity of a probe will not be significantly attenuated if 80% or more of the base sequence is consecutively conserved. It can therefore be concluded, from the finding, such that any sequences modified from the probe sequences disclosed in the specification will have a sufficient probe function if 80% or more of the base sequence of the probe is consecutively conserved.

The above-mentioned modified sequences may include any variation as far as it does not impair the probe's function, or any variation as far as it hybridizes with a nucleic acid sequence of interest as a detection target. Above all, it is desirable to include any variation as far as it can hybridize with a nucleic acid sequence of interest as a detection target under stringent conditions. Preferable hybridization conditions confining the variation include those represented in examples as described below. Here, the term "detection target" used herein may be one included in a sample to be used in hybridization, which may be a unique base sequence to the infectious disease pathogenic bacterium, or may be a complementary sequence to the unique sequence. Further, the variation may be a modified sequence obtained by deletion, substitution, or addition of at least one base as far as it retains a function as the probe.

Those probe sequences are only specific to the DNA sequence coding for the 16S rRNA of the above-mentioned bacterium, so sufficient hybridization sensitivity to the sequence will be expected even under stringent conditions. In addition, any of those probe sequences forms a stable hybridized product through a hybridization reaction thereof with a target analyte even when the probe sequences are immobilized on a carrier, which is designed to produce an excellent result.

Further, a probe-immobilized carrier (e.g., DNA chip), on which the probe for detecting the infectious disease pathogenic bacterium of the present invention, can be obtained by supplying the probe on a predetermined position on the carrier and immobilizing the probe thereon. Various methods can be used for supplying the probe to the carrier. Among them, for example, a method, which can be suitably used, is to keep a surface state capable of immobilizing the probe on the carrier through a chemical bonding (e.g., covalent bonding) and a liquid containing the probe is then provided on a predetermined position by an inkjet method. Such a method allows the probe to be hardly detached from the carrier and exerts an additional effect of improving the sensitivity. In other words, when a stamping method conventionally used and called the Stanford method is employed to make a DNA chip, the resultant DNA chip has a disadvantage such that the applied DNA tends to be peeled off. Another one of the methods of forming DNA chips is to carry out the arrangement of probes by the synthesis of DNA on the surface of a carrier (e.g., DNA chip from Affymetrix Co., Ltd.). In such a method of synthesizing probes on a carrier, it is difficult to make equal the amount of synthesized DNA for each probe sequence. Thus, the amount of immobilized probe per immobilization area (spot) for each probe tends to vary considerably. Such variations in amounts of the respective immobilized probes may cause incorrect evaluation on the results of the detection with those probes. Based on this fact, the probe carrier of the present invention is preferably prepared using the above-mentioned inkjet method. The inkjet method as described above has an advantage such that the probe can be stably immobilized on the carrier and hardly detaching from the carrier to efficiently provide a probe carrier which can carry out detection with high sensitivity and high accuracy.

In addition, a probe set may include at least two selected from the group consisting of SEQ ID NOS. 81 to 83 as described above and the complementary sequences thereof and sequences obtained by base deletion, substitution, or addition on those sequences as far as they retain the function of a probe for detecting the gene of *Peptococcus niger*. In this case, the accuracy of detecting the *Peptococcus niger* gene can be further improved.

Hereinafter, preferred embodiments of the present invention will be described in detail.

Test objects to be tested using probe carriers (e.g., DNA chips) in which the probes of the present invention are immobilized on carriers include those originated from humans and animals such as domestic animals. For example, a test object is any of those which may contain bacteria, including: any body fluids such as blood, cerebrospinal fluid, expectorated sputum, gastric juice, vaginal discharge, and oral mucosal fluid; and excretions such as urine and feces. All media, which can be contaminated with bacteria, can be also subjected to a test using a DNA chip. Such media include: food, drink water and water in the natural environment such as hot spring water, which may cause food poisoning by contamination; filters of air cleaners and the like; and so on. Animals and plants, which should be quarantined in import/export, are also used as analytes of interest.

When the sample as described above can be directly used in reaction with the DNA chip, it is used as an analyte to react with the DNA chip and the result of the reaction is then analyzed. Alternatively, when the sample cannot be directly reacted with the DNA chip, the sample was subjected to extraction, purification, and other procedures for obtaining a target substance if required and then provided as an analyte to carry out a reaction with the DNA chip. For instance, when the sample contains a target nucleic acid, an extract, which may be assumed to contain such a target nucleic acid, is prepared from a sample, and then washed, diluted, or the like to obtain an analyte solution followed by reaction with the DNA chip. Further, as a target nucleic acid is included in an analyte obtained by carrying out various amplification procedures such as PCR amplification, the target nucleic acid may be amplified and then reacted with a DNA chip. Such analytes of amplified nucleic acids include the following ones: (a) An amplified analyte prepared by using a PCR-reaction primer designed for detecting 16S rRNA gene. (b) An amplified analyte prepared by an additional PCR reaction or the like from a PCR-amplified product. (c) An analyte prepared by an amplification method other than PCR. (d) An analyte labeled for visualization by any of various labeling methods.

Further, a carrier used for preparing a probe-immobilized carrier, such as a DNA chip, may be any of those that satisfy the property of carrying out a solid phase/liquid phase reaction of interest. Examples of the carrier include: flat substrates such as a glass substrate, a plastic substrate, and a silicon wafer; a three-dimensional structure having an irregular surface; and a spherical body such as a bead, and rod-, cord-, and thread-shaped structures. The surface of the carrier may be processed such that a probe can be immobilized thereon. Especially, a carrier prepared by introducing a functional group to its surface to enable chemical reaction has a preferable form from the viewpoint of reproducibility because the probe is stably bonded in the process of hybridization reaction.

Various methods can be employed for the immobilization of probes. An example of such a method is to use a combination of a maleimide group and a thiol (—SH) group. In this method, a thiol (—SH) group is bonded to the terminal of a probe, and a process is executed in advance to make the carrier (solid) surface have a maleimide group. Accordingly, the thiol group of the probe supplied to the carrier surface reacts with the maleimide group on the carrier surface to form a covalent bond, whereby the probe is immobilized.

Introduction of the maleimide group can utilize a process of firstly allowing a reaction between a glass substrate and an aminosilane coupling agent and then introducing a maleimide group onto the glass substrate by a reaction of the amino group with an EMCS reagent (N-(6-maleimidocaproyloxy) succinimide, available from Dojindo). Introduction of the thiol group to a DNA can be carried out using 5'-Thiol-Modifier C6 (available from Glen Research) when the DNA is synthesized by an automatic DNA synthesizer.

Instead of the above-described combination of a thiol group and a maleimide group, a combination of, e.g., an epoxy group (on the solid phase) and an amino group (nucleic acid probe terminal), can also be used as a combination of functional groups to be used for immobilization. Surface treatments using various kinds of silane coupling agents are also effective. A probe in which a functional group which can react with a functional group introduced by a silane coupling agent is introduced is used. A method of applying a resin having a functional group can also be used.

The detection of the gene of the infectious disease pathogenic bacterium by using the probe-immobilized carrier of the present invention can be carried out by a genetic testing method including the steps of: (i) reacting an analyte with a probe-immobilized carrier on which the probe of the present invention is immobilized; (ii) detecting the presence or absence of the reaction of a nucleic acid in the analyte with the probe on the probe-immobilized carrier, or detecting the strength of the hybridization reaction of a nucleic acid in the analyte with the probe on the probe-immobilized carrier; and (iii) specifying the probe having reacted with the nucleic acid in the analyte when the reaction of the probe with the nucleic acid in the analyte is detected and specifying the gene of the infectious disease pathogenic bacterium in the analyte based on the nucleic acid sequence of the probe.

The probe to be immobilized on the probe-immobilized carrier is at least one of the above-mentioned items (A) to (L). On the carrier, probes for detecting bacterial species other than *Peptococcus niger* may be immobilized as other probes, depending on the purpose of test. In this case, the other probes may be those capable of detecting the bacterial species other than *Peptococcus niger* without causing cross contamination and the use of such probes allows simultaneous detection of a plurality of bacterial species with high accuracy.

Further, as described above, when the 16S rRNA gene sequence of an infectious disease pathogenic bacterium in the analyte is amplified by PCR and provided as a sample to be reacted with a probe carrier, a primer set for detecting the infectious disease pathogenic bacterium can be used. The primer set suitably includes at least one selected from oligonucleotides represented in the following items (1) to (21) and at least one selected from oligonucleotides represented in the following items (22) to (28), more suitably includes all the oligonucleotides represented in the following items (1) to (28):

(1) an oligonucleotide having a base sequence of
5' gcggcgtgcctaatacatgcaag 3'; (SEQ ID NO: 1)

(2) an oligonucleotide having a base sequence of
5' gcggcaggcctaacacatgcaag 3'; (SEQ ID NO: 2)

(3) an oligonucleotide having a base sequence of
5' gcggcaggcttaacacatgcaag 3'; (SEQ ID NO: 3)

(4) an oligonucleotide having a base sequence of
5' gcggtaggcctaacacatgcaag 3'; (SEQ ID NO: 4)

-continued (5) an oligonucleotide having a base sequence of
5' gcggcgtgcttaacacatgcaag 3';  (SEQ ID NO: 5)

(6) an oligonucleotide having a base sequence of
5' gcgggatgccttacacatgcaag 3';  (SEQ ID NO: 6)

(7) an oligonucleotide having a base sequence of
5' gcggcatgccttacacatgcaag 3';  (SEQ ID NO: 7)

(8) an oligonucleotide having a base sequence of
5' gcggcatgcttaacacatgcaag 3';  (SEQ ID NO: 8)

(9) an oligonucleotide having a base sequence of
5' gcggcgtgcttaatacatgcaag 3';  (SEQ ID NO: 9)

(10) an oligonucleotide having a base sequence of
5' gcggcaggcctaatacatgcaag 3';  (SEQ ID NO: 10)

(11) an oligonucleotide having a base sequence of
5' gcgggatgctttacacatgcaag 3';  (SEQ ID NO: 11)

(12) an oligonucleotide having a base sequence of
5' gcggcgtgcctaacacatgcaag 3';  (SEQ ID NO: 12)

(13) an oligonucleotide having a base sequence of
5' gcggcgtgcataacacatgcaag 3';  (SEQ ID NO: 13)

(14) an oligonucleotide having a base sequence of
5' gcggcatgcctaacacatgcaag 3';  (SEQ ID NO: 14)

(15) an oligonucleotide having a base sequence of
5' gcggcgcgcctaacacatgcaag 3';  (SEQ ID NO: 15)

(16) an oligonucleotide having a base sequence of
5' gcggcgcgcttaacacatgcaag 3';  (SEQ ID NO: 16)

(17) an oligonucleotide having a base sequence of
5' gcgtcatgcctaacacatgcaag 3';  (SEQ ID NO: 17)

(18) an oligonucleotide having a base sequence of
5' gcgataggcttaacacatgcaag 3';  (SEQ ID NO: 18)

(19) an oligonucleotide having a base sequence of
5' gcgacaggcttaacacatgcaag 3';  (SEQ ID NO: 19)

(20) an oligonucleotide having a base sequence of
5' gctacaggcttaacacatgcaag 3';  (SEQ ID NO: 20)

(21) an oligonucleotide having a base sequence of
5' acagaatgcttaacacatgcaag 3';  (SEQ ID NO: 21)

(22) an oligonucleotide having a base sequence of
5' atccagccgcaccttccgatac 3';  (SEQ ID NO: 22)

(23) an oligonucleotide having a base sequence of
5' atccaaccgcaggttcccctac 3';  (SEQ ID NO: 23)

(24) an oligonucleotide having a base sequence of
5' atccagccgcaggttcccctac 3';  (SEQ ID NO: 24)

(25) an oligonucleotide having a base sequence of
5' atccagccgcaccttccggtac 3';  (SEQ ID NO: 25)

(26) an oligonucleotide having a base sequence of
5' atccagcgccaggttcccctag 3';  (SEQ ID NO: 26)

(27) an oligonucleotide having a base sequence of
5' atccagccgcaggttctcctac 3';  (SEQ ID NO: 27)
and

(28) an oligonucleotide having a base sequence of
5' atccagccgcacgttcccgtac 3'.  (SEQ ID NO: 28)

Among them, a primer designed for allowing the amplification of *Peptococcus niger* is a primer set of the following:
(14) an oligonucleotide having a base sequence of 5' gcggcatgcctaacacatgcaag 3' (SEQ ID NO: 14); and
(22) an oligonucleotide having a base sequence of 5' atccagccgcaccttccgatac 3' (SEQ ID NO: 22).

For detecting *Peptococcus niger*, at least such a primer may be included.

The utilities of the respective primers (1) to (28) for amplification of *Peptococcus niger* (ATCC 27731) can be evaluated and confirmed by comparing each sequence of SEQ ID NOs. 1 to 28 with a DNA sequence including the 16S rRNA coding region of *Peptococcus niger* (SEQ ID NO. 95).

A kit for detecting the infectious disease pathogenic bacterium can be constructed using at least a probe as described above and a reagent for detecting a reaction of the probe with a nucleic acid in an analyte. The probe in the kit can preferably be provided as a probe-immobilized carrier as described above. Further, the detection reagent may contain a label to detect the reaction or a primer for carrying out amplification as a pre-treatment.

EXAMPLES

Hereinafter, the present invention will be described in more detail with reference to examples using probes for detecting an infectious disease pathogenic bacterium to detect *Peptococcus niger*.

Example 1

In this example, microorganism detection using 2-step PCR will be described.

1. Preparation of Probe DNA

Nucleic acid sequences shown in Table 1 were designed as probes to be used for detection of *Peptococcus niger*. Specifically, the following probe base sequences were selected from the genome part coding for the 16s rRNA gene of *Peptococcus niger*. These probe base sequences were designed such that they could have an extremely high specificity to the bacterium, and a sufficient hybridization sensitivity could be expected without variance for the respective probe base sequences. The probe base sequences need not always completely match with those shown in Table 1. Probes having base lengths of 20 to 30 which include the base sequences shown in Table 1 can also be used, in addition to the probes having the base sequences shown in Table 1. However, it should be ensured that the other portion of the base sequence than the portion shown in Table 1 in such a probe has no effect on the detection accuracy.

TABLE 1

Name of microorganism
*Peptococcus niger*

| Probe No. | SEQ ID NO. | Sequence |
|---|---|---|
| 114_G_PEP_01 | 81 | 5' GTACCTGTAAGAAAGACGGCCTTCGT 3' |
| 114_G_PEP_02 | 82 | 5' CTGCCGAGTGATGTAATGTCACTTTTC 3' |
| 114_G_PEP_03 | 83 | 5' TCGGAGGTTTCAAGACCGTCGG 3' |

For each probe having a base sequence shown in Table 1, a thiol group was introduced, as a functional group to immobilize the probe on a DNA chip, to the 5' terminal of the nucleic acid after synthesis in accordance with a conventional method. After introduction of the functional group, purification and freeze-drying were executed. The freeze-dried probes for internal standard were stored in a freezer at −30° C.

2. Preparation of PCR Primers 2-1. Preparation of PCR Primers for Analyte Amplification As 16S rRNA gene (target gene) amplification PCR primers for pathogenic bacterium detection, nucleic acid sequences shown in Table 2 below were designed. Specifically, primer sets which specifically amplify the genome parts coding the 16S rRNAs, i.e., primers for which the specific melting points were made uniform as far as possible at the two end portions of the 16S rRNA coding region of a base length of 1,400 to 1,700 were designed. In order to simultaneously amplify a plurality of different bacterial species listed in the following items (1) to (80), mutants, or a plurality of 16S rRNA genes on genomes, a plurality of kinds of primers were designed. Note that a primer set is not limited to the primer sets shown in Table 2 as far as the primer set is available in common to amplify almost the entire lengths of the 16S rRNA genes of the pathogenic bacteria.

TABLE 2

| Primer No | SEQ ID NO. | Sequence |
|---|---|---|
| F01 | 1 | 5' GCGGCGTGCCTAATACATGCAAG 3' |
| F02 | 2 | 5' GCGGCAGGCCTAACACATGCAAG 3' |
| F03 | 3 | 5' GCGGCAGGCTTAACACATGCAAG 3' |
| F04 | 4 | 5' GCGGTAGGCCTAACACATGCAAG 3' |
| F05 | 5 | 5' GCGGCGTGCTTAACACATGCAAG 3' |
| F06 | 6 | 5' GCGGGATGCCTTACACATGCAAG 3' |
| F07 | 7 | 5' GCGGCATGCCTTACACATGCAAG 3' |
| F08 | 8 | 5' GCGGCATGCTTAACACATGCAAG 3' |
| F09 | 9 | 5' GCGGCGTGCTTAATACATGCAAG 3' |
| F10 | 10 | 5' GCGGCAGGCCTAATACATGCAAG 3' |
| F11 | 11 | 5' GCGGGATGCTTTACACATGCAAG 3' |
| F12 | 12 | 5' GCGGCGTGCCTAACACATGCAAG 3' |
| F13 | 13 | 5' GCGGCGTGCATAACACATGQAAG 3' |
| F14 | 14 | 5' GCGGCATOCCTAACACATGCAAG 3' |
| F15 | 15 | 5' GCGGCGCGCCTAACACATGCAAG 3' |
| F16 | 16 | 5' GCGGCGCGCTTAACACATGCAAG 3' |
| F17 | 17 | 5' GCGTCATGCCTAACACATGCAAG 3' |
| F18 | 18 | 5' GCGATAGGCTTAACACATGCAAG 3' |
| F19 | 19 | 5' GCGACAGGCTTAACACATGCAAG 3' |
| F20 | 20 | 5' GCTACAGGCTTAACACATGCAAG 3' |
| F21 | 21 | 5' ACAGAATGCTTAACACATGCAAG 3' |
| R01 | 22 | 5' ATCCAGCCGCACCTTCCGATAC 3' |
| R02 | 23 | 5' ATCCAACCGCAGCTTCCCCTAC 3' |
| R03 | 24 | 5' ATCCAGCCGCAGGTTCCCCTAC 3' |
| R04 | 25 | 5' ATCCAGCCGCACCTTCCGGTAC 3' |
| R05 | 26 | 5' ATCCAGCGCCAGGTTCCCCTAG 3' |
| R06 | 27 | 5' ATCCAGCCGCAGGTTCTCCTAC 3' |
| R07 | 28 | 5' ATCCAGCCGCACGTTCCCGTAC 3' |

(1) *Staphylococcus aureus*
(2) *Staphylococcus epidermidis*
(3) *Escherichia coli*
(4) *Klebsiella pneumoniae*
(5) *Pseudomonas aeruginosa*
(6) *Serratia marcescens*
(7) *Streptococcus pneumoniae*
(8) *Haemophilus influenzae*
(9) *Enterobacter cloacae*
(10) *Enterococcus faecalis*
(11) *Staphylococcus haemolyticus*
(12) *Staphylococcus hominis*
(13) *Staphylococcus saprophyticus*
(14) *Streptococcus agalactiae*
(15) *Streptococcus mutans*
(16) *Streptococcus pyogenes*
(17) *Streptococcus sanguinis*
(18) *Enterococcus avium*
(19) *Enterococcus faecium*
(20) *Pseudomonas fluorescens*
(21) *Pseudomonas putida*
(22) *Burkholderia cepacia*
(23) *Stenotrophomonas maltophilia*
(24) *Acinetobacter baumannii*
(25) *Acinetobacter calcoaceticus*
(26) *Achromobacter xylosoxidans*
(27) *Vibrio vulnificus*
(28) *Salmonella choleraesuis*
(29) *Citrobacter freundii*
(30) *Klebsiella oxytoca*
(31) *Enterobacter aerogenes*
(32) *Hafnia alvei*
(33) *Serratia liquefaciens*
(34) *Proteus mirabilis*
(35) *Proteus vulgaris*
(36) *Morganella morganii*
(37) *Providencia rettgeri*
(38) *Aeromonas hydrophila*
(39) *Aeromonas sobria*
(40) *Gardnerella vaginalis*
(41) *Corynebacterium diphtheriae*
(42) *Legionella pneumophila*
(43) *Bacillus cereus*
(44) *Bacillus subtilis*
(45) *Mycobacterium kansasii*
(46) *Mycobacterium intracellulare*
(47) *Mycobacterium chelonae*
(48) *Nocardia asteroides*
(49) *Bacteroides fragilis*
(50) *Bacteroides thetaiotaomicron*
(51) *Clostridium difficile*
(52) *Clostridium perfringens*
(53) *Eggerthella lenta*
(54) *Fusobacterium necrophorum*
(55) *Fusobacterium nucleatum*
(56) *Lactobacillus acidophilus*
(57) *Anaerococcus prevotii*
(58) *Peptoniphilus asaccharolyticus*
(59) *Porphyromonas asaccharolytica*
(60) *Porphyromonas gingivalis*
(61) *Prevotella denticola*
(62) *Propionibacterium acnes*
(63) *Acinetobacter johnsonii*
(64) *Acinetobacter junii*
(65) *Aeromonas schubertii*
(66) *Aeromonas veronii*
(67) *Bacteroides distasonis*
(68) *Bacteroides vulgatus*
(69) *Campylobacter coli*
(70) *Campylobacter hyointestinalis*
(71) *Campylobacter jejuni*

(72) *Flavobacterium aquatile*
(73) *Flavobacterium mizutaii*
(74) *Peptococcus niger*
(75) *Propionibacterium avidum*
(76) *Propionibacterium freudenreichii*
(77) *Propionibacterium granulosum*
(78) *Clostridium butyricum*
(79) *Flavobacterium hydatis*
(80) *Flavobacterium johnsoniae*

The primers shown in Table 2 were purified by high performance liquid chromatography (HPLC) after synthesis. The twenty-one forward primers and the seven reverse primers were mixed and dissolved in a TE buffer solution such that each primer concentration had an ultimate concentration of 10 pmol/µl.

2-2. Preparation of Labeling PCR Primers

In a manner similar to the above-mentioned analyte amplification primers, oligonucleotides having sequences as shown in Table 3 below were employed as primers for labeling.

TABLE 3

| Primer No | SEQ ID NO. | Sequence |
| --- | --- | --- |
| Cy3R9-1 | 29 | 5' TACCTTGTTACGACTTCACCCCA 3' |
| Cy3R9-2 | 30 | 5' TACCTTGTTACGACTTCGTCCCA 3' |
| Cy3R9-3 | 31 | 5' TACCTTGTTACGACTTAGTCCCA 3' |
| Cy3R9-4 | 32 | 5' TACCTTGTTACGACTTAGCCCCA 3' |
| Cy3R9-5 | 33 | 5' TACCTTGTTACGACTTAGTCCTA 3' |
| Cy3R9-6 | 34 | 5' TACCTTGTTACGACTTAGCCCTA 3' |

The primers shown in Table 3 were labeled with a fluorescent dye, Cy3. The primers were purified by high performance liquid chromatography (HPLC) after synthesis. The six labeled primers were mixed and dissolved in a TE buffer solution such that each primer concentration had an ultimate concentration of 10 pmol/µl.

3. Extraction of Genome DNA (Model Analyte) of *Peptococcus niger*

3-1. Microbial Culture & Genome DNA Extraction

First, *Peptococcus niger* (ATCC 27731) was cultured in accordance with the conventional method. This microbial culture medium was subjected to the extraction and purification of genome DNA by using a nucleic acid purification kit (FastPrep FP100A FastDNA Kit, manufactured by Funakoshi Co., Ltd.).

3-2. Test of Collected Genome DNA

The collected genome DNA of the microorganism, *Peptococcus niger*, was subjected to agarose electrophoresis and 260/280-nm absorbance determination in accordance with the conventional method. Thus, the quality (the admixture amount of low molecular nucleic acid and the degree of decomposition) and the collection amount were tested. In this example, about 10 µg of the genome DNA was collected. No degradation of genome DNA or contamination of rRNA was observed. The collected genome DNA was dissolved in a TE buffer solution at an ultimate concentration of 50 ng/µl and used in the following experiments.

4. Preparation of DNA Chip 4-1. Cleaning of Glass Substrate

A glass substrate (size: 25 mm×75 mm×1 mm, available from Iiyama Precision Glass) made of synthetic quartz was placed in a heat- and alkali-resisting rack and dipped in a cleaning solution for ultrasonic cleaning, which was adjusted to have a predetermined concentration. The glass substrate was kept dipped in the cleaning solution for a night and cleaned by ultrasonic cleaning for 20 min. The substrate was picked up, lightly rinsed with pure water, and cleaned by ultrasonic cleaning in ultrapure water for 20 min. The substrate was dipped in a 1N aqueous sodium hydroxide solution heated to 80° C. for 10 min. Pure water cleaning and ultrapure water cleaning were executed again. A quartz glass substrate for a DNA chip was thus prepared.

4-2. Surface Treatment

A silane coupling agent KBM-603 (available from Shin-Etsu Silicone) was dissolved in pure water at a concentration of 1% by weight (wt %) and stirred at room temperature for 2 hrs. The cleaned glass substrate was dipped in the aqueous solution of the silane coupling agent and left stand still at room temperature for 20 min. The glass substrate was picked up. The surface thereof was lightly rinsed with pure water and dried by spraying nitrogen gas to both surfaces of the substrate. The dried substrate was baked in an oven at 120° C. for 1 hr to complete the coupling agent treatment, whereby an amino group was introduced to the substrate surface. Next, N-maleimidocaproyloxy succinimido (abbreviated as EMCS hereinafter) was dissolved in a 1:1 (volume ratio) solvent mixture of dimethyl sulfoxide and ethanol to obtain an ultimate concentration of 0.3 mg/ml. As a result, an EMCS solution was prepared. Here, EMCS is N-(6-maleimidocaproyloxy)succinimido available from Dojindo.

The baked glass substrate was left stand and cooled and dipped in the prepared EMCS solution at room temperature for 2 hrs. By this treatment, the amino group introduced to the surface of the substrate by the silane coupling agent reacted with the succinimide group in the EMCS to introduce the maleimide group to the surface of the glass substrate. The glass substrate picked up from the EMCS solution was cleaned by using the above-described solvent mixture in which the EMCS was dissolved. The glass substrate was further cleaned by ethanol and dried in a nitrogen gas atmosphere.

4-3. Probe DNA

The microorganism detection probe prepared in the stage 1 (Preparation of Probe DNA) of Example 1 was dissolved in pure water. The solution was dispensed such that the ultimate concentration (at ink dissolution) became 10 µM. Then, the solution was freeze-dried to remove water.

4-4. DNA Discharge by BJ Printer and Bonding to Substrate

An aqueous solution containing 7.5-wt % glycerin, 7.5-wt % thiodiglycol, 7.5-wt % urea, and 1.0-wt % Acetylenol EH (available from Kawaken Fine Chemicals) was prepared. Each of the three probes (Table 1) prepared in advance was dissolved in the solvent mixture at a specific concentration. An ink tank for an inkjet printer (trade name: BJF-850, available from Canon) is filled with the resultant DNA solution and attached to the printhead.

The inkjet printer used here was modified in advance to allow printing on a flat plate. When a printing pattern is input in accordance with a predetermined file creation method, about 5-picoliter of a DNA solution can be spotted at a pitch of about 120 µm.

The printing operation was executed for one glass substrate by using the modified inkjet printer to prepare an array. After confirming that printing was reliably executed, the glass substrate was left stand still in a humidified chamber for 30 min to make the maleimide group on the glass substrate surface react with the thiol group at the nucleic acid probe terminal.

4-5. Cleaning

After reaction for 30 min, the DNA solution remaining on the surface was cleaned by using a 10-mM phosphate buffer (pH 7.0) containing 100-mM NaCl, thereby obtaining a DNA chip in which single-stranded DNAs were immobilized on the glass substrate surface.

5. Amplification and Labeling of Analyte 5-1. Amplification of Analyte: 1st PCR

The amplification reaction (1st PCR) and the labeling reaction (2nd PCR) of a microbial gene to be provided as an analyte are shown in Table 4 below.

TABLE 4

| | |
|---|---|
| AmpliTaq Gold LD (5.0 U/μL) | 0.5 μL (2.5 unit/tube) |
| Primer mix <FR21x7> | 2.0 μL |
| Forward primer (x21 [0.625 μM/each]) | (final 1.25 pmol each/tube) |
| Reverse primer (x07 [1.875 μM/each]) | (final 3.75 pmol each/tube) |
| 10x PCR buffer | 5.0 μL (final 1x conc.) |
| $MgCl_2$ (25 mM) | 8.0 μL (final 4.0 mM) |
| dNTPmix (2.5 mM/each) | 4.0 μL (final 200 μM each) |
| Template | variable |
| $H_2O$ | up to 50 μL |
| Total | 50 μL |

Amplification reaction of the reaction solution having the above-mentioned composition was carried out using a commercially available thermal cycler in accordance with the protocol illustrated in FIG. 1. After the end of reaction, the primer was purified using a purification column (QIAquick PCR Purification Kit available from QIAGEN). Subsequently, the quantitative assay of the amplified product was carried out.

5-2. Labeling Reaction: 2nd PCR

Figure 2:
FIG. 2 is a diagram illustrating a 2nd PCR protocol.

Amplification reaction of the reaction solution having the composition shown in Table 5 was carried out using a commercially available thermal cycler in accordance with the protocol illustrated in FIG. 2.

TABLE 5

| | |
|---|---|
| Premix Taq (Ex Taq Version) | 25 μL |
| Cy3-labeled reverse primer mix | 0.83 μL |
| Cy3R9 mix (x06[10 μM/each]) | (final 8.3 pmol each/tube) |
| Template | variable (final 30 ng/tube) |
| $H_2O$ | up to 50 μL |
| Total | 50 μL |

After the end of reaction, the primer was purified using a purification column (QIAquick PCR Purification Kit available from QIAGEN) to obtain a labeled analyte.

6. Hybridization

Detection reaction was performed using the DNA chip prepared in the stage 4 (Preparation of DNA Chip) and the labeled analyte prepared in the stage 5 (Amplification and Labeling of Analyte).

6-1. Blocking of DNA Chip

Bovine serum albumin (BSA, Fraction V: available from Sigma) was dissolved in a 100-mM NaCl/10-mM phosphate buffer such that a 1 wt % solution was obtained. Then, the DNA chip prepared in the stage 4 (Preparation of DNA Chip) was dipped in the solution at room temperature for 2 hrs to execute blocking. After the end of blocking, the chip was cleaned using a washing solution as described below, rinsed with pure water and hydro-extracted by a spin dryer.

The washing solution: 2×SSC solution (NaCl 300 mM, sodium citrate (trisodium citrate dihydrate, $C_6H_5Na_3.2H_2O$) 30 mM, pH 7.0) containing 0.1-wt % sodium dodecyl sulfate (SDS)

6-2. Hybridization

The hydro-extracted DNA chip was placed in a hybridization apparatus (Hybridization Station available from Genomic Solutions Inc). Hybridization reaction was carried out in a hybridization solution under conditions as described below.

6-3. Hybridization Solution

6×SSPE/10% formamide/target (all 2nd PCR products)/ 0.05 wt % (6×SSPE: NaCl 900 mM, $NaH_2PO_4H_2O$ 50 mM, EDTA 6 mM, pH, 7.4)

6-4. Hybridization Conditions

65° C. for 3 min, 55° C. for 4 hrs, washing with 2×SSC/ 0.1% SDS at 50° C., washing with 2×SSC/0.1% SDS at 20° C. (rinse with $H_2O$: manual), and spin dry.

7. Microorganism Genome Detection (Fluorometry)

The DNA chip after the end of hybridization reaction was subjected to fluorometry with a DNA chip fluorescent detector (GenePix 4000B available from Axon). As a result, *Peptococcus niger* was able to be detected with a sufficient signal at a high reproducibility. The results of fluorometry are shown in Table 6 below.

TABLE 6

| Probe No. | Fluorescence intensity<br>*Peptococcus niger* (ATCC 27731) |
|---|---|
| 114_G_PEP_01 | 2439.4 |
| 114_G_PEP_02 | 11226.4 |
| 114_G_PEP_03 | 4068.7 |

8. Hybridization with Other Bacterial Species

For proving the fact that the probe set shown in Table 1 can be specifically hybridized only with *Peptococcus niger*, the results of hybridization reaction with *Escherichia coli* (JCM 1649) are shown in Table 7 below.

TABLE 7

| Probe No. | Fluorescence intensity<br>*Escherichia coli* (JCM 1649) |
|---|---|
| 114_G_PEP_01 | 50.0 |
| 114_G_PEP_02 | 50.1 |
| 114_G_PEP_03 | 50.1 |

9. Results

As is evident from the above description, a DNA chip was prepared such that a probe set, which was able to detect only *Peptococcus niger* in a specific manner, was immobilized. Further, the use of such a DNA chip allowed the identification of an infectious disease pathogenic bacterium, so the problems of the DNA probe derived from a microorganism was able to be solved. In other words, the oligonucleotide probe can be chemically produced in large amounts, while the purification or concentration thereof can be controlled. In addition, for classification of microbial species, a probe set capable of collectively detecting bacterial strains of the same genus and differentially detecting them from bacteria of other genera, was able to be provided.

Further, in addition to *Escherichia coli* as described above, hybridization reaction was carried out on each of nucleic acids extracted from the bacteria represented in the above-mentioned items (1) to (80). The results thereof confirmed that no substantial reaction was observed with respect to each of those bacteria in a manner similar to that of *Escherichia coli*, except of *Peptococcus niger*.

The bacteria represented in the above-mentioned items (1) to (80) are pathogenic bacteria for septicemia, and they cover almost all of the pathogenic bacteria ever detected in human blood. Therefore, by using the primer of the present embodiment, the nucleic acid of an infectious disease pathogenic bacterium in blood can be extracted and then subjected to hybridization reaction with the probe of the present invention, whereby identification of *Peptococcus niger* can be performed with higher accuracy.

Further, according to the above-mentioned example, the presence of an infectious disease pathogenic bacterium can be efficiently determined with high accuracy by completely detecting the 16S rRNA gene from the gene of the infectious disease pathogenic bacterium.

Example 2

Preparation of DNA Chip by which Various bacterial species can be simultaneously determined In a manner similar to the stage 1 (Preparation of Probe DNA) of Example 1, probes having base sequences as shown in Table 8 below were prepared.

TABLE 8

| Bacterial species (or genus) of interest | Probe sequence (5'→3') | SEQ ID NO. |
|---|---|---|
| *Anaerococcus prevotii* | TCATCTTGAGGTATGGAAGGGAAAGTGG | 36 |
| | GTGTTAGGTGTCTGGAATAATCTGGGTG | |
| | ACCAAGTCTTGACATATTACGGCGG | 37 |
| *Bacteroides fragilis* | AAGGATTCCGGTAAAGGATGGGGATG | 38 |
| | TGGAAACATGTCAGTGAGCAATCACC | 39 |
| *Bacteroides thetaiotaomicron* | AAGAATTTCGGTTATCGATGGGGATGC | 40 |
| | AAGTTTTCCACGTGTGGAATTTTGTATGT | 41 |
| | AAGGCAGCTACCTGGTGACAGGAT | 42 |
| *Clostridium difficile* | AATATCAAAGGTGAGCCAGTACAGGATGGA | 43 |
| | CCGTAGTAAGCTCTTGAAACTGGGAGAC | 44 |
| | TCCCAATGACATCTCCTTAATCGGAGAG | 45 |
| *Clostridium perfringens* | AACCAAAGGAGCAATCCGCTATGAGAT | 46 |
| | GAGCGTAGGCGGATGATTAAGTGGG | 47 |
| | CCCTTGCATTACTCTTAATCGAGGAAATC | 48 |
| *Eggerthella lenta* | GGAAAGCCCAGACGGCAAGGGA | 49 |
| | CCTCTCAAGCGGGATCTCTAATCCGA | 50 |
| | TGCCCCATGTTGCCAGCATTAGG | 51 |
| *Fusobacterium necrophorum* | TTTTCGCATGGAGGAATCATGAAAGCTA | 52 |
| | AGATGCGCCGGTGCCCTTTCG | 53 |
| | AGTCGGGAAGAAGTCAGTGACGGTAC | 54 |
| *Peptoniphilus asaccharolyticus* | GAGTACGTGCGCAAGCATGAAACT | 55 |
| *Porphyromonas asaccharolytica* | GAAGACTGCCCGCAAGGGTTGTAA | 56 |
| | GTGTACTGGAGGTACGTGGAACGTG | 57 |
| | GCATGAGGCTGAGAGGTCTCTTCC | 58 |
| *Porphyromonas gingivalis* | TTATAGCTGTAAGATAGGCATGCGTCCC | 59 |
| | AACGGGCGATACGAGTATTGCATTGA | 60 |
| | ATATACCGTCAAGCTTCCACAGCGA | 61 |
| *Enterococcus avium* | TTTGAAAGGCGCTTTTGCGTCACTG | 62 |
| | CAAGGATGAGAGTAGAACGTTCATCCCTTG | 63 |
| | CAAGGATGAGAGTAGAATGTTCATCCCTTG | 64 |
| *Providencia rettgeri* | CCTGGGAATGGCATCTAAGACTGGTCA | 65 |
| | GAGGAAGGCGTTGATGCTAATATCATCA | 66 |
| | GAGCAAAGCAGGGAACTTCGGTC | 67 |
| *Acinetobacter* (genus) | GTTGGGGCCTTTGAGGCTTTAGTG | 68 |
| | TGGGAGAGGATGGTAGAATTCCAGGT | 69 |
| *Prevotella denticola* | TCGATGACGGCATCAGATTCGAAGCA | 70 |
| | AATGTAGGCGCCCAACGTCTGACT | 71 |
| | ATGTTGAGGTCCTTCGGGACTCCT | 72 |
| *Flavobacterium* (genus) | GGAAGTAACTAGAATATGTAGTGTAGCGGTG | 73 |
| | GCCAGTGCAAACTGTGAGGAAGGT | 74 |
| | GGGTAGGGGTCCTGAGAGGGAGATC | 75 |
| *Aeromonas* (genus) | GAGTGCCTTCGGGAATCAGAACAC | 76 |
| | CTGCAAGCTAGCGATAGTGAGCGA | 77 |
| *Bacteroides* (genus) | CGATGGATAGGGGTTCTGAGAGGAA | 78 |
| | TGCGGCTCAACCGTAAAATTGCAGT | 79 |
| | TGTGGCTCAACCATAGAATTGCCGT | 80 |

TABLE 8-continued

| Bacterial species (or genus) of interest | Probe sequence (5'→3') | SEQ ID NO. |
|---|---|---|
| Peptocoocus niger | GTACCTGTAAGAAAGACGGCCTTCGT | 81 |
| | CTGCCGAGTGATGTAATGTCACTTTTC | 82 |
| | TCGGAGGTTTCAAGACCGTCGG | 83 |
| Clostridium(genus) | ACCAAAGGAGCAATCCGCTATGAGATG | 84 |
| | ATCAAAGGTGAGCCAGTACAGGATGG | 85 |
| | ATTAAAGGAGTAATCCGCTATGAGATGGACC | 86 |
| Propionibacterium acnes | GGGCTAATACCGGATAGGAGCTCCTG | 87 |
| | AAGCGTGAGTGACGGTAATGGGTAAA | 88 |
| | ATCGCGTCGGAAGTGTAATCTTGGG | 89 |
| Campylobacter(genus) | TGGAGCAAATCTATAAAATATGTCCCAGT | 90 |
| | ACAGTGGAATCAGCGACTGGGG | 91 |
| Aeromonas hydrophila | GCCTAATACGTATCAACTGTGACGTTAC | 92 |
| | GCCTAATACGTGTCAACTGTGACGTTAC | 93 |
| Propionibacterium (genus) | GCTTTCGATACGGGTTGACTTGAGGAA | 94 |

Those probes are capable of specifically detecting certain bacterial species (or genera) shown in the left column in the table just as one specific to *Peptococcus niger* of Example 1.

Further, those probes are designed such that they have the same Tm value as that of a target, the same reactivity with a non-target sequence, and the like so that the nucleic acid of the bacterial species of interest can be specifically detected under the same reaction conditions.

For the respective probes, probe solutions were prepared in a manner similar to the stage 4-3 of Example 1. Subsequently, the inkjet printer used in the stage 4-4 of Example 1 was employed to discharge each of the probe solution on the same substrate to form a plurality of DNA chips having spots of the respective probes being arranged at a pitch of about 120 μm.

One of the DNA chips was used for hybridization with the nucleic acid extracted from *Peptococcus niger* in a manner similar to the stage 6 of Example 1. As a result, the spot of the probe which specifically detected *Peptococcus niger* showed almost the equal fluorescence intensity as that of Example 1. In contrast, the spots of other probes showed extremely low fluorescence intensity.

Further, other prepared DNA chips were used for hybridization with the bacteria listed in Table 8 except of *Peptococcus niger*. As a result, the spot of *Peptococcus niger* showed extremely low fluorescence intensity, while the spot of the probe for the bacterial species of interest showed extremely high fluorescence intensity. Therefore, the DNA chip prepared in the present example was confirmed that it was able to simultaneously determine 15 bacterial species and 7 genera listed in Table 8 in addition to *Peptococcus niger*. By simultaneously using probes for a target species and the corresponding genus (for example, *Propionibacterium* (genus) and *Propionibacterium acnes*), highly accurate identification of the target species or simultaneous identification of a plurality of target species of the same genus can be performed.

Example 3

Using the DNA chip prepared in Example 2, detection was attempted when a plurality of bacterial species was present in an analyte.

A culture medium in which *Peptococcus niger* and *Eggerthella lenta* were cultured was prepared and subjected to the same treatment as that of Example 1 to react with the DNA chip.

As a result, only the spots of the probes having SEQ ID NOS. 49, 50, 51, 81, 82, and 83 showed high fluorescence intensity, so the coexistence of those bacteria was able to be simultaneously confirmed.

The present invention is not limited to the above-mentioned embodiments and various changes and modifications can be made within the spirit and scope of the present invention. Therefore to apprise the public of the scope of the present invention, the following claims are made.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2006-306006, filed Nov. 10, 2006, which is hereby incorporated by reference herein in its entirety.

What is claimed is:

1. A probe set for detecting a gene of infectious disease pathogenic bacterium, *Peptococcus niger*, comprising three probes consisting of the following base sequences (1) to (3) respectively:
   (1) GTACCTGTAAGAAAGACGGCCTTCGT (SEQ ID NO. 81) or the complementary sequence thereof;
   (2) CTGCCGAGTGATGTAATGTCACTTTTC (SEQ ID NO. 82) or the complementary sequence thereof; and
   (3) TCGGAGGTTTCAAGACCGTCGG (SEQ ID NO. 83) or the complementary sequence thereof.

2. A probe-immobilized carrier, wherein at least the probe set according to claim 1 is arranged on a solid-phase carrier.

3. A probe-immobilized carrier according to claim 2, wherein the probe-immobilized carrier further comprises at least one probe having any one of the base sequences of SEQ ID NOS. 35 to 94 immobilized at a position spaced from the probe set.

4. A kit for detecting a gene of *Peptococcus niger*, comprising:
   a probe set according to claim 1; and
   a reagent for detecting a reaction between the probe set and a target nucleic acid.

5. A kit according to claim 4, wherein the reagent contains a primer for amplifying the gene of *Peptococcus niger*, and the primer includes:
   an oligonucleotide having the base sequence of 5' gcggcatgcctaacacatgcaag 3' (SEQ ID NO: 14); and
   an oligonucleotide having the base sequence of 5' atccagccgcaccttccgatac 3' (SEQ ID NO: 22).

6. A gene detection kit, comprising:

a probe-immobilized carrier according to claim 3; and a reagent for detecting a reaction between the probes and a target nucleic acid, wherein the reagent contains a primer including at least one oligonucleotide selected from the following items (1) to (21) and at least one oligonucleotide selected from the following items (22) to (28):

```
(1) an oligonucleotide having a base sequence of
5' gcggcgtgcctaatacatgcaag 3';   (SEQ ID NO: 1)

(2) an oligonucleotide having a base sequence of
5' gcggcaggcctaacacatgcaag 3';   (SEQ ID NO: 2)

(3) an oligonucleotide having a base sequence of
5' gcggcaggcttaacacatgcaag 3';   (SEQ ID NO: 3)

(4) an oligonucleotide having a base sequence of
5' gcggtaggcctaacacatgcaag 3';   (SEQ ID NO: 4)

(5) an oligonucleotide having a base sequence of
5' gcggcgtgcttaacacatgcaag 3';   (SEQ ID NO: 5)

(6) an oligonucleotide having a base sequence of
5' gcgggatgccttacacatgcaag 3';   (SEQ ID NO: 6)

(7) an oligonucleotide having a base sequence of
5' gcggcatgccttacacatgcaag 3';   (SEQ ID NO: 7)

(8) an oligonucleotide having a base sequence of
5' gcggcatgcttaacacatgcaag 3';   (SEQ ID NO: 8)

(9) an oligonucleotide having a base sequence of
5' gcggcgtgcttaatacatgcaag 3';   (SEQ ID NO: 9)

(10) an oligonucleotide having a base sequence of
5' gcggcaggcctaatacatgcaag 3';   (SEQ ID NO: 10)

(11) an oligonucleotide having a base sequence of
5' gcgggatgctttacacatgcaag 3';   (SEQ ID NO: 11)

(12) an oligonucleotide having a base sequence of
5' gcggcgtgcctaacacatgcaag 3';   (SEQ ID NO: 12)

(13) an oligonucleotide having a base sequence of
5' gcggcgtgcataacacatgcaag 3';   (SEQ ID NO: 13)

(14) an oligonucleotide having a base sequence of
5' gcggcatgcctaacacatgcaag 3';   (SEQ ID NO: 14)

(15) an oligonucleotide having a base sequence of
5' gcggcgcgcctaacacatgcaag 3';   (SEQ ID NO: 15)

(16) an oligonucleotide having a base sequence of
5' gcggcgcgcttaacacatgcaag 3';   (SEQ ID NO: 16)

(17) an oligonucleotide having a base sequence of
5' gcgtcatgcctaacacatgcaag 3';   (SEQ ID NO: 17)

(18) an oligonucleotide having a base sequence of
5' gcgataggcttaacacatgcaag 3';   (SEQ ID NO: 18)

(19) an oligonucleotide having a base sequence of
5' gcgacaggcttaacacatgcaag 3';   (SEQ ID NO: 19)

(20) an oligonucleotide having a base sequence of
5' gctacaggcttaacacatgcaag 3';   (SEQ ID NO: 20)

(21) an oligonucleotide having a base sequence of
5' acagaatgcttaacacatgcaag 3';   (SEQ ID NO: 21)

(22) an oligonucleotide having a base sequence of
5' atccagccgcaccttccgatac 3';    (SEQ ID NO: 22)

(23) an oligonucleotide having a base sequence of
5' atccaaccgcaggttccccctac 3';   (SEQ ID NO: 23)

(24) an oligonucleotide having a base sequence of
5' atccagccgcaggttcccctac 3';    (SEQ ID NO: 24)

(25) an oligonucleotide having a base sequence of
5' atccagccgcaccttccggtac 3';    (SEQ ID NO: 25)

(26) an oligonucleotide having a base sequence of
5' atccagcgccaggttcccctag 3';    (SEQ ID NO: 26)

(27) an oligonucleotide having a base sequence of
5' atccagccgcaggttctcctac 3';    (SEQ ID NO: 27)
and

(28) an oligonucleotide having a base sequence of
5' atccagccgcacgttcccgtac 3'.    (SEQ ID NO: 28)
```

7. A probe set for detecting a gene of infectious disease pathogenic bacterium, *Peptococcus niger*, including the following items (A) to (C), wherein the probe set does not comprise any other probe to detect *Peptococcus niger*:

```
(A) a probe consisting of the base sequence of
GTACCTGTAAGAAAGACGGCCTTCGT;     (SEQ ID NO. 81)

(B) a probe consisting of the base sequence of
CTGCCGAGTGATGTAATGTCACTTTTC;    (SEQ ID NO. 82)
and (C) a probe consisting of the base sequence of
TCGGAGGTTTCAAGACCGTCGG          (SEQ ID NO. 83).
```

8. A probe-immobilized carrier according to claim 2, wherein the probe set comprises the following items (A) to (C):

```
(A) a probe consisting of the base sequence of
GTACCTGTAAGAAAGACGGCCTTCGT;     (SEQ ID NO. 81)

(B) a probe consisting of the base sequence of
CTGCCGAGTGATGTAATGTCACTTTTC;    (SEQ ID NO. 82)
and (C) a probe consisting of the base sequence of
TCGGAGGTTTCAAGACCGTCGG          (SEQ ID NO. 83).
```

9. A probe-immobilized carrier according to claim 8, wherein the probe-immobilized carrier comprises at least one probe having any one of the base sequences of SEQ ID NOS. 35 to 94 immobilized at a position spaced from the probe set.

10. A method of detecting a gene of *Peptococcus niger* in an analyte by using a probe-immobilized carrier, comprising the steps of:
   (i) reacting the analyte with a probe-immobilized carrier according to claim 2; and
   (ii) detecting the presence or absence of a reaction of the probe set on the probe-immobilized carrier with a nucleic acid in the analyte, or detecting the strength of a hybridization reaction of the probe set on the probe-immobilized carrier with the nucleic acid in the analyte.

11. A method according to claim 10, further comprising the step of carrying out PCR amplification of the nucleic acid in the analyte by using a primer including the following oligonucleotides:

```
an oligonucleotide having the base sequence of
5'gcggcatgcctaacacatgcaag 3';    (SEQ ID NO: 14)
and an oligonucleotide having the base sequence of
5'atccagccgcaccttccgatac 3'      (SEQ ID NO: 22).
```

\* \* \* \* \*

SEQUENCE LISTING

<160> NUMBER OF SEQ ID NOS: 95

<210> SEQ ID NO 1
<211> LENGTH: 23
<212> TYPE: DNA
<213> ORGANISM: Artificial
<220> FEATURE:
<223> OTHER INFORMATION: Primer

```
<400> SEQUENCE: 1
gcggcgtgcc taatacatgc aag                                          23

<210> SEQ ID NO 2
<211> LENGTH: 23
<212> TYPE: DNA
<213> ORGANISM: artificial
<220> FEATURE:
<223> OTHER INFORMATION: Primer

<400> SEQUENCE: 2
gcggcaggcc taacacatgc aag                                          23

<210> SEQ ID NO 3
<211> LENGTH: 23
<212> TYPE: DNA
<213> ORGANISM: artificial
<220> FEATURE:
<223> OTHER INFORMATION: Primer

<400> SEQUENCE: 3
gcggcaggct taacacatgc aag                                          23

<210> SEQ ID NO 4
<211> LENGTH: 23
<212> TYPE: DNA
<213> ORGANISM: artificial
<220> FEATURE:
<223> OTHER INFORMATION: Primer

<400> SEQUENCE: 4
gcggtaggcc taacacatgc aag                                          23

<210> SEQ ID NO 5
<211> LENGTH: 23
<212> TYPE: DNA
<213> ORGANISM: artificial
<220> FEATURE:
<223> OTHER INFORMATION: Primer

<400> SEQUENCE: 5
gcggcgtgct taacacatgc aag                                          23

<210> SEQ ID NO 6
<211> LENGTH: 23
<212> TYPE: DNA
<213> ORGANISM: artificial
<220> FEATURE:
<223> OTHER INFORMATION: Primer

<400> SEQUENCE: 6
gcgggatgcc ttacacatgc aag                                          23

<210> SEQ ID NO 7
<211> LENGTH: 23
<212> TYPE: DNA
<213> ORGANISM: artificial
<220> FEATURE:
<223> OTHER INFORMATION: Primer

<400> SEQUENCE: 7
gcggcatgcc ttacacatgc aag                                          23

<210> SEQ ID NO 8
<211> LENGTH: 23
<212> TYPE: DNA
```

-continued

```
<213> ORGANISM: artificial
<220> FEATURE:
<223> OTHER INFORMATION: Primer

<400> SEQUENCE: 8
gcggcatgct taacacatgc aag                                              23

<210> SEQ ID NO 9
<211> LENGTH: 23
<212> TYPE: DNA
<213> ORGANISM: artificial
<220> FEATURE:
<223> OTHER INFORMATION: Primer

<400> SEQUENCE: 9
gcggcgtgct taatacatgc aag                                              23

<210> SEQ ID NO 10
<211> LENGTH: 23
<212> TYPE: DNA
<213> ORGANISM: artificial
<220> FEATURE:
<223> OTHER INFORMATION: Primer

<400> SEQUENCE: 10
gcggcaggcc taatacatgc aag                                              23

<210> SEQ ID NO 11
<211> LENGTH: 23
<212> TYPE: DNA
<213> ORGANISM: artificial
<220> FEATURE:
<223> OTHER INFORMATION: Primer

<400> SEQUENCE: 11
gcgggatgct ttacacatgc aag                                              23

<210> SEQ ID NO 12
<211> LENGTH: 23
<212> TYPE: DNA
<213> ORGANISM: artificial
<220> FEATURE:
<223> OTHER INFORMATION: Primer

<400> SEQUENCE: 12
gcggcgtgcc taacacatgc aag                                              23

<210> SEQ ID NO 13
<211> LENGTH: 23
<212> TYPE: DNA
<213> ORGANISM: artificial
<220> FEATURE:
<223> OTHER INFORMATION: Primer

<400> SEQUENCE: 13
gcggcgtgca taacacatgc aag                                              23

<210> SEQ ID NO 14
<211> LENGTH: 23
<212> TYPE: DNA
<213> ORGANISM: artificial
<220> FEATURE:
<223> OTHER INFORMATION: Primer

<400> SEQUENCE: 14
gcggcatgcc taacacatgc aag                                              23
```

```
<210> SEQ ID NO 15
<211> LENGTH: 23
<212> TYPE: DNA
<213> ORGANISM: artificial
<220> FEATURE:
<223> OTHER INFORMATION: Primer

<400> SEQUENCE: 15
gcggcgcgcc taacacatgc aag                                              23

<210> SEQ ID NO 16
<211> LENGTH: 23
<212> TYPE: DNA
<213> ORGANISM: artificial
<220> FEATURE:
<223> OTHER INFORMATION: Primer

<400> SEQUENCE: 16
gcggcgcgct taacacatgc aag                                              23

<210> SEQ ID NO 17
<211> LENGTH: 23
<212> TYPE: DNA
<213> ORGANISM: artificial
<220> FEATURE:
<223> OTHER INFORMATION: Primer

<400> SEQUENCE: 17
gcgtcatgcc taacacatgc aag                                              23

<210> SEQ ID NO 18
<211> LENGTH: 23
<212> TYPE: DNA
<213> ORGANISM: artificial
<220> FEATURE:
<223> OTHER INFORMATION: Primer

<400> SEQUENCE: 18
gcgataggct taacacatgc aag                                              23

<210> SEQ ID NO 19
<211> LENGTH: 23
<212> TYPE: DNA
<213> ORGANISM: artificial
<220> FEATURE:
<223> OTHER INFORMATION: Primer

<400> SEQUENCE: 19
gcgacaggct taacacatgc aag                                              23

<210> SEQ ID NO 20
<211> LENGTH: 23
<212> TYPE: DNA
<213> ORGANISM: artificial
<220> FEATURE:
<223> OTHER INFORMATION: Primer

<400> SEQUENCE: 20
gctacaggct taacacatgc aag                                              23

<210> SEQ ID NO 21
<211> LENGTH: 23
<212> TYPE: DNA
<213> ORGANISM: artificial
<220> FEATURE:
<223> OTHER INFORMATION: Primer
```

```
<400> SEQUENCE: 21
acagaatgct taacacatgc aag                                              23

<210> SEQ ID NO 22
<211> LENGTH: 22
<212> TYPE: DNA
<213> ORGANISM: artificial
<220> FEATURE:
<223> OTHER INFORMATION: Primer

<400> SEQUENCE: 22
atccagccgc accttccgat ac                                               22

<210> SEQ ID NO 23
<211> LENGTH: 22
<212> TYPE: DNA
<213> ORGANISM: artificial
<220> FEATURE:
<223> OTHER INFORMATION: Primer

<400> SEQUENCE: 23
atccaaccgc aggttcccct ac                                               22

<210> SEQ ID NO 24
<211> LENGTH: 22
<212> TYPE: DNA
<213> ORGANISM: artificial
<220> FEATURE:
<223> OTHER INFORMATION: Primer

<400> SEQUENCE: 24
atccagccgc aggttcccct ac                                               22

<210> SEQ ID NO 25
<211> LENGTH: 22
<212> TYPE: DNA
<213> ORGANISM: artificial
<220> FEATURE:
<223> OTHER INFORMATION: Primer

<400> SEQUENCE: 25
atccagccgc accttccggt ac                                               22

<210> SEQ ID NO 26
<211> LENGTH: 22
<212> TYPE: DNA
<213> ORGANISM: artificial
<220> FEATURE:
<223> OTHER INFORMATION: Primer

<400> SEQUENCE: 26
atccagcgcc aggttcccct ag                                               22

<210> SEQ ID NO 27
<211> LENGTH: 22
<212> TYPE: DNA
<213> ORGANISM: artificial
<220> FEATURE:
<223> OTHER INFORMATION: Primer

<400> SEQUENCE: 27
atccagccgc aggttctcct ac                                               22

<210> SEQ ID NO 28
<211> LENGTH: 22
<212> TYPE: DNA
```

```
<213> ORGANISM: artificial
<220> FEATURE:
<223> OTHER INFORMATION: Primer

<400> SEQUENCE: 28
atccagccgc acgttcccgt ac                                              22

<210> SEQ ID NO 29
<211> LENGTH: 23
<212> TYPE: DNA
<213> ORGANISM: artificial
<220> FEATURE:
<223> OTHER INFORMATION: Primer

<400> SEQUENCE: 29
taccttgtta cgacttcacc cca                                             23

<210> SEQ ID NO 30
<211> LENGTH: 23
<212> TYPE: DNA
<213> ORGANISM: artificial
<220> FEATURE:
<223> OTHER INFORMATION: Primer

<400> SEQUENCE: 30
taccttgtta cgacttcgtc cca                                             23

<210> SEQ ID NO 31
<211> LENGTH: 23
<212> TYPE: DNA
<213> ORGANISM: artificial
<220> FEATURE:
<223> OTHER INFORMATION: Primer

<400> SEQUENCE: 31
taccttgtta cgacttagtc cca                                             23

<210> SEQ ID NO 32
<211> LENGTH: 23
<212> TYPE: DNA
<213> ORGANISM: artificial
<220> FEATURE:
<223> OTHER INFORMATION: Primer

<400> SEQUENCE: 32
taccttgtta cgacttagcc cca                                             23

<210> SEQ ID NO 33
<211> LENGTH: 23
<212> TYPE: DNA
<213> ORGANISM: artificial
<220> FEATURE:
<223> OTHER INFORMATION: Primer

<400> SEQUENCE: 33
taccttgtta cgacttagtc cta                                             23

<210> SEQ ID NO 34
<211> LENGTH: 23
<212> TYPE: DNA
<213> ORGANISM: artificial
<220> FEATURE:
<223> OTHER INFORMATION: Primer

<400> SEQUENCE: 34
taccttgtta cgacttagcc cta                                             23
```

<210> SEQ ID NO 35
<211> LENGTH: 28
<212> TYPE: DNA
<213> ORGANISM: Artificial
<220> FEATURE:
<223> OTHER INFORMATION: probe

<400> SEQUENCE: 35
tcatcttgag gtatggaagg gaaagtgg                                28

<210> SEQ ID NO 36
<211> LENGTH: 28
<212> TYPE: DNA
<213> ORGANISM: artificial
<220> FEATURE:
<223> OTHER INFORMATION: probe

<400> SEQUENCE: 36
gtgttaggtg tctggaataa tctgggtg                                28

<210> SEQ ID NO 37
<211> LENGTH: 25
<212> TYPE: DNA
<213> ORGANISM: artificial
<220> FEATURE:
<223> OTHER INFORMATION: probe

<400> SEQUENCE: 37
accaagtctt gacatattac ggcgg                                   25

<210> SEQ ID NO 38
<211> LENGTH: 26
<212> TYPE: DNA
<213> ORGANISM: artificial
<220> FEATURE:
<223> OTHER INFORMATION: probe

<400> SEQUENCE: 38
aaggattccg gtaaaggatg gggatg                                  26

<210> SEQ ID NO 39
<211> LENGTH: 26
<212> TYPE: DNA
<213> ORGANISM: artificial
<220> FEATURE:
<223> OTHER INFORMATION: probe

<400> SEQUENCE: 39
tggaaacatg tcagtgagca atcacc                                  26

<210> SEQ ID NO 40
<211> LENGTH: 27
<212> TYPE: DNA
<213> ORGANISM: artificial
<220> FEATURE:
<223> OTHER INFORMATION: probe

<400> SEQUENCE: 40
aagaatttcg gttatcgatg gggatgc                                 27

<210> SEQ ID NO 41
<211> LENGTH: 29
<212> TYPE: DNA
<213> ORGANISM: artificial
<220> FEATURE:
<223> OTHER INFORMATION: probe

<400> SEQUENCE: 41
aagttttcca cgtgtggaat tttgtatgt                              29

<210> SEQ ID NO 42
<211> LENGTH: 24
<212> TYPE: DNA
<213> ORGANISM: artificial
<220> FEATURE:
<223> OTHER INFORMATION: probe

<400> SEQUENCE: 42
aaggcagcta cctggtgaca ggat                                   24

<210> SEQ ID NO 43
<211> LENGTH: 30
<212> TYPE: DNA
<213> ORGANISM: artificial
<220> FEATURE:
<223> OTHER INFORMATION: probe

<400> SEQUENCE: 43
aatatcaaag gtgagccagt acaggatgga                             30

<210> SEQ ID NO 44
<211> LENGTH: 28
<212> TYPE: DNA
<213> ORGANISM: artificial
<220> FEATURE:
<223> OTHER INFORMATION: probe

<400> SEQUENCE: 44
ccgtagtaag ctcttgaaac tgggagac                               28

<210> SEQ ID NO 45
<211> LENGTH: 28
<212> TYPE: DNA
<213> ORGANISM: artificial
<220> FEATURE:
<223> OTHER INFORMATION: probe

<400> SEQUENCE: 45
tcccaatgac atctccttaa tcggagag                               28

<210> SEQ ID NO 46
<211> LENGTH: 27
<212> TYPE: DNA
<213> ORGANISM: artificial
<220> FEATURE:
<223> OTHER INFORMATION: probe

<400> SEQUENCE: 46
aaccaaagga gcaatccgct atgagat                                27

<210> SEQ ID NO 47
<211> LENGTH: 25
<212> TYPE: DNA
<213> ORGANISM: artificial
<220> FEATURE:
<223> OTHER INFORMATION: probe

<400> SEQUENCE: 47
gagcgtaggc ggatgattaa gtggg                                  25

<210> SEQ ID NO 48
<211> LENGTH: 29
<212> TYPE: DNA

<213> ORGANISM: artificial
<220> FEATURE:
<223> OTHER INFORMATION: probe

<400> SEQUENCE: 48
cccttgcatt actcttaatc gaggaaatc					29

<210> SEQ ID NO 49
<211> LENGTH: 22
<212> TYPE: DNA
<213> ORGANISM: artificial
<220> FEATURE:
<223> OTHER INFORMATION: probe

<400> SEQUENCE: 49
ggaaagccca gacggcaagg ga					22

<210> SEQ ID NO 50
<211> LENGTH: 26
<212> TYPE: DNA
<213> ORGANISM: artificial
<220> FEATURE:
<223> OTHER INFORMATION: probe

<400> SEQUENCE: 50
cctctcaagc gggatctcta atccga					26

<210> SEQ ID NO 51
<211> LENGTH: 23
<212> TYPE: DNA
<213> ORGANISM: artificial
<220> FEATURE:
<223> OTHER INFORMATION: probe

<400> SEQUENCE: 51
tgccccatgt tgccagcatt agg					23

<210> SEQ ID NO 52
<211> LENGTH: 28
<212> TYPE: DNA
<213> ORGANISM: artificial
<220> FEATURE:
<223> OTHER INFORMATION: probe

<400> SEQUENCE: 52
ttttcgcatg gaggaatcat gaaagcta					28

<210> SEQ ID NO 53
<211> LENGTH: 21
<212> TYPE: DNA
<213> ORGANISM: artificial
<220> FEATURE:
<223> OTHER INFORMATION: probe

<400> SEQUENCE: 53
agatgcgccg gtgccctttc g					21

<210> SEQ ID NO 54
<211> LENGTH: 26
<212> TYPE: DNA
<213> ORGANISM: artificial
<220> FEATURE:
<223> OTHER INFORMATION: probe

<400> SEQUENCE: 54
agtcgggaag aagtcagtga cggtac					26

<210> SEQ ID NO 55
<211> LENGTH: 24
<212> TYPE: DNA
<213> ORGANISM: artificial
<220> FEATURE:
<223> OTHER INFORMATION: probe

<400> SEQUENCE: 55
gagtacgtgc gcaagcatga aact                                          24

<210> SEQ ID NO 56
<211> LENGTH: 24
<212> TYPE: DNA
<213> ORGANISM: artificial
<220> FEATURE:
<223> OTHER INFORMATION: probe

<400> SEQUENCE: 56
gaagactgcc cgcaagggtt gtaa                                          24

<210> SEQ ID NO 57
<211> LENGTH: 25
<212> TYPE: DNA
<213> ORGANISM: artificial
<220> FEATURE:
<223> OTHER INFORMATION: probe

<400> SEQUENCE: 57
gtgtactgga ggtacgtgga acgtg                                         25

<210> SEQ ID NO 58
<211> LENGTH: 24
<212> TYPE: DNA
<213> ORGANISM: artificial
<220> FEATURE:
<223> OTHER INFORMATION: probe

<400> SEQUENCE: 58
gcatgaggct gagaggtctc ttcc                                          24

<210> SEQ ID NO 59
<211> LENGTH: 28
<212> TYPE: DNA
<213> ORGANISM: artificial
<220> FEATURE:
<223> OTHER INFORMATION: probe

<400> SEQUENCE: 59
ttatagctgt aagataggca tgcgtccc                                      28

<210> SEQ ID NO 60
<211> LENGTH: 26
<212> TYPE: DNA
<213> ORGANISM: artificial
<220> FEATURE:
<223> OTHER INFORMATION: probe

<400> SEQUENCE: 60
aacgggcgat acgagtattg cattga                                        26

<210> SEQ ID NO 61
<211> LENGTH: 25
<212> TYPE: DNA
<213> ORGANISM: artificial
<220> FEATURE:
<223> OTHER INFORMATION: probe

```
<400> SEQUENCE: 61
atataccgtc aagcttccac agcga                                            25

<210> SEQ ID NO 62
<211> LENGTH: 25
<212> TYPE: DNA
<213> ORGANISM: artificial
<220> FEATURE:
<223> OTHER INFORMATION: probe

<400> SEQUENCE: 62
tttgaaaggc gcttttgcgt cactg                                            25

<210> SEQ ID NO 63
<211> LENGTH: 30
<212> TYPE: DNA
<213> ORGANISM: artificial
<220> FEATURE:
<223> OTHER INFORMATION: probe

<400> SEQUENCE: 63
caaggatgag agtagaacgt tcatcccttg                                       30

<210> SEQ ID NO 64
<211> LENGTH: 30
<212> TYPE: DNA
<213> ORGANISM: artificial
<220> FEATURE:
<223> OTHER INFORMATION: probe

<400> SEQUENCE: 64
caaggatgag agtagaatgt tcatcccttg                                       30

<210> SEQ ID NO 65
<211> LENGTH: 27
<212> TYPE: DNA
<213> ORGANISM: artificial
<220> FEATURE:
<223> OTHER INFORMATION: probe

<400> SEQUENCE: 65
cctgggaatg gcatctaaga ctggtca                                          27

<210> SEQ ID NO 66
<211> LENGTH: 28
<212> TYPE: DNA
<213> ORGANISM: artificial
<220> FEATURE:
<223> OTHER INFORMATION: probe

<400> SEQUENCE: 66
gaggaaggcg ttgatgctaa tatcatca                                         28

<210> SEQ ID NO 67
<211> LENGTH: 24
<212> TYPE: DNA
<213> ORGANISM: artificial
<220> FEATURE:
<223> OTHER INFORMATION: probe

<400> SEQUENCE: 67
gagcaaagca ggggaacttc ggtc                                             24

<210> SEQ ID NO 68
<211> LENGTH: 24
<212> TYPE: DNA
```

```
<213> ORGANISM: artificial
<220> FEATURE:
<223> OTHER INFORMATION: probe

<400> SEQUENCE: 68
gttggggcct ttgaggcttt agtg                                           24

<210> SEQ ID NO 69
<211> LENGTH: 26
<212> TYPE: DNA
<213> ORGANISM: artificial
<220> FEATURE:
<223> OTHER INFORMATION: probe

<400> SEQUENCE: 69
tgggagagga tggtagaatt ccaggt                                         26

<210> SEQ ID NO 70
<211> LENGTH: 26
<212> TYPE: DNA
<213> ORGANISM: artificial
<220> FEATURE:
<223> OTHER INFORMATION: probe

<400> SEQUENCE: 70
tcgatgacgg catcagattc gaagca                                         26

<210> SEQ ID NO 71
<211> LENGTH: 24
<212> TYPE: DNA
<213> ORGANISM: artificial
<220> FEATURE:
<223> OTHER INFORMATION: probe

<400> SEQUENCE: 71
aatgtaggcg cccaacgtct gact                                           24

<210> SEQ ID NO 72
<211> LENGTH: 24
<212> TYPE: DNA
<213> ORGANISM: artificial
<220> FEATURE:
<223> OTHER INFORMATION: probe

<400> SEQUENCE: 72
atgttgaggt ccttcgggac tcct                                           24

<210> SEQ ID NO 73
<211> LENGTH: 31
<212> TYPE: DNA
<213> ORGANISM: artificial
<220> FEATURE:
<223> OTHER INFORMATION: probe

<400> SEQUENCE: 73
ggaagtaact agaatatgta gtgtagcggt g                                   31

<210> SEQ ID NO 74
<211> LENGTH: 24
<212> TYPE: DNA
<213> ORGANISM: artificial
<220> FEATURE:
<223> OTHER INFORMATION: probe

<400> SEQUENCE: 74
gccagtgcaa actgtgagga aggt                                           24
```

```
<210> SEQ ID NO 75
<211> LENGTH: 25
<212> TYPE: DNA
<213> ORGANISM: artificial
<220> FEATURE:
<223> OTHER INFORMATION: probe

<400> SEQUENCE: 75
gggtaggggt cctgagaggg agatc                                              25

<210> SEQ ID NO 76
<211> LENGTH: 24
<212> TYPE: DNA
<213> ORGANISM: artificial
<220> FEATURE:
<223> OTHER INFORMATION: probe

<400> SEQUENCE: 76
gagtgccttc gggaatcaga acac                                               24

<210> SEQ ID NO 77
<211> LENGTH: 24
<212> TYPE: DNA
<213> ORGANISM: artificial
<220> FEATURE:
<223> OTHER INFORMATION: probe

<400> SEQUENCE: 77
ctgcaagcta gcgatagtga gcga                                               24

<210> SEQ ID NO 78
<211> LENGTH: 25
<212> TYPE: DNA
<213> ORGANISM: artificial
<220> FEATURE:
<223> OTHER INFORMATION: probe

<400> SEQUENCE: 78
cgatggatag gggttctgag aggaa                                              25

<210> SEQ ID NO 79
<211> LENGTH: 25
<212> TYPE: DNA
<213> ORGANISM: artificial
<220> FEATURE:
<223> OTHER INFORMATION: probe

<400> SEQUENCE: 79
tgcggctcaa ccgtaaaatt gcagt                                              25

<210> SEQ ID NO 80
<211> LENGTH: 25
<212> TYPE: DNA
<213> ORGANISM: artificial
<220> FEATURE:
<223> OTHER INFORMATION: probe

<400> SEQUENCE: 80
tgtggctcaa ccatagaatt gccgt                                              25

<210> SEQ ID NO 81
<211> LENGTH: 26
<212> TYPE: DNA
<213> ORGANISM: artificial
<220> FEATURE:
<223> OTHER INFORMATION: probe
```

-continued

```
<400> SEQUENCE: 81
gtacctgtaa gaaagacggc cttcgt                                            26

<210> SEQ ID NO 82
<211> LENGTH: 27
<212> TYPE: DNA
<213> ORGANISM: artificial
<220> FEATURE:
<223> OTHER INFORMATION: probe

<400> SEQUENCE: 82
ctgccgagtg atgtaatgtc acttttc                                           27

<210> SEQ ID NO 83
<211> LENGTH: 22
<212> TYPE: DNA
<213> ORGANISM: artificial
<220> FEATURE:
<223> OTHER INFORMATION: probe

<400> SEQUENCE: 83
tcggaggttt caagaccgtc gg                                                22

<210> SEQ ID NO 84
<211> LENGTH: 27
<212> TYPE: DNA
<213> ORGANISM: artificial
<220> FEATURE:
<223> OTHER INFORMATION: probe

<400> SEQUENCE: 84
accaaaggag caatccgcta tgagatg                                           27

<210> SEQ ID NO 85
<211> LENGTH: 26
<212> TYPE: DNA
<213> ORGANISM: artificial
<220> FEATURE:
<223> OTHER INFORMATION: probe

<400> SEQUENCE: 85
atcaaaggtg agccagtaca ggatgg                                            26

<210> SEQ ID NO 86
<211> LENGTH: 31
<212> TYPE: DNA
<213> ORGANISM: artificial
<220> FEATURE:
<223> OTHER INFORMATION: probe

<400> SEQUENCE: 86
attaaaggag taatccgcta tgagatggac c                                      31

<210> SEQ ID NO 87
<211> LENGTH: 26
<212> TYPE: DNA
<213> ORGANISM: artificial
<220> FEATURE:
<223> OTHER INFORMATION: probe

<400> SEQUENCE: 87
gggctaatac cggataggag ctcctg                                            26

<210> SEQ ID NO 88
<211> LENGTH: 26
<212> TYPE: DNA
```

```
<213> ORGANISM: artificial
<220> FEATURE:
<223> OTHER INFORMATION: probe

<400> SEQUENCE: 88
aagcgtgagt gacggtaatg ggtaaa                                              26

<210> SEQ ID NO 89
<211> LENGTH: 25
<212> TYPE: DNA
<213> ORGANISM: artificial
<220> FEATURE:
<223> OTHER INFORMATION: probe

<400> SEQUENCE: 89
atcgcgtcgg aagtgtaatc ttggg                                              25

<210> SEQ ID NO 90
<211> LENGTH: 29
<212> TYPE: DNA
<213> ORGANISM: artificial
<220> FEATURE:
<223> OTHER INFORMATION: probe

<400> SEQUENCE: 90
tggagcaaat ctataaaata tgtcccagt                                          29

<210> SEQ ID NO 91
<211> LENGTH: 22
<212> TYPE: DNA
<213> ORGANISM: artificial
<220> FEATURE:
<223> OTHER INFORMATION: probe

<400> SEQUENCE: 91
acagtggaat cagcgactgg gg                                                 22

<210> SEQ ID NO 92
<211> LENGTH: 28
<212> TYPE: DNA
<213> ORGANISM: artificial
<220> FEATURE:
<223> OTHER INFORMATION: probe

<400> SEQUENCE: 92
gcctaatacg tatcaactgt gacgttac                                           28

<210> SEQ ID NO 93
<211> LENGTH: 28
<212> TYPE: DNA
<213> ORGANISM: artificial
<220> FEATURE:
<223> OTHER INFORMATION: probe

<400> SEQUENCE: 93
gcctaatacg tgtcaactgt gacgttac                                           28

<210> SEQ ID NO 94
<211> LENGTH: 27
<212> TYPE: DNA
<213> ORGANISM: artificial
<220> FEATURE:
<223> OTHER INFORMATION: probe

<400> SEQUENCE: 94
gctttcgata cgggttgact tgaggaa                                            27
```

```
<210> SEQ ID NO 95
<211> LENGTH: 1529
<212> TYPE: DNA
<213> ORGANISM: Peptococcus niger

<400> SEQUENCE: 95
ctcaggacaa acgctggcgg catgcctaac acatgcaagt cgaacggacg gaggaaagag      60
atctcttcgg agtgaccttt cccgagttag tggcggatgg gtgagtaacg cgtgagtgac     120
ctgcccagca gtggggaata acagtgagaa atcattgcta ataccgcata ccttacaagt     180
gctccatggt acctgtaaga aagacggcct tcgtgctgtc gctgttggat ggactcgcgt     240
ctgattagcc agttggtggg gtaacggcct accaaagcaa tgatcagtag ccggcctgag     300
agggtgaacg gccacattgg gactgagaca cggcccaaac tcctacggga ggcagcagtg     360
gggaatcttc cgcaatgggc gcaagcctga cggagcaatg ccgcgtgagt gaagaaggcc     420
ttcgggttgt aaaactctgt cctcatccaa gagagagacc tgtagtaact gccaggtcta     480
ggacggtaga tgaggaggaa gccccggcta actatgtgcc agcagccgcg gtaaaacata     540
gggggcaagc gttgtccgga atcactgggc gtaaagggcg cgcaggcggt ctgttaagtc     600
agatgtgaaa ggttagggct caaccctgaa cgtgcatctg atactggcag acttgagtat     660
ggaagaggta agtggaattc ctagtgtagc ggtgaaatgc gtagatatta ggaggaacac     720
cagtggcgaa ggcgacttac tgggccataa ctgacgctga ggcgcgaaag cgtggggagc     780
aaactggatt agataccctg gtagtccacg ccgtaaacga tgggtactag gtgtcggagg     840
tttcaagacc gtcggtgccg cagttaacac aataagtacc ccgcctgggg agtacggtcg     900
caagactgaa actcaaagga attgacgggg gcccgcacaa gcggtggagc atgtggttta     960
attcgacgca acgcgaagaa ccttaccaag acttgacatc ctgctgccga gtgatgtaat    1020 gtcactttc cttcgggaca gcagagacag gtggtgcatg gttgtcgtca gctcgtgtcg    1080
tgagatgttg ggttaagtcc cgcaacgagc gcaacccttg tcgtcagttg ccatcattaa    1140
gttgggcact ctgacgagac tgccgcagac aatgcggagg aaggtgggga tgacgtcaaa    1200
tcatcatgcc ccttatgtct tgggctacac acgtgctaca atggtcggta cagagggcag    1260
cgaaggagcg atccggagcg aatctcacaa agccgatccc agttcggatt gcaggctgca    1320
actcgcctgc atgaagtcgg aatcgctagt aatcgcaggt cagcatactg cggtgaatac    1380
gttcccgggc cttgtacaca ccgcccgtca caccacgaaa gttggtaaca cccgaagtcg    1440
gtgatctgac cttttaggag gaagccgccc acggtgggat cgatgattgg ggtgaagtcg    1500
taacaaggta gccgtatcgg aaggtgcgg                                      1529
```